United States Patent [19]

Mention et al.

[11] Patent Number: 5,229,134
[45] Date of Patent: Jul. 20, 1993

[54] PHARMACEUTICAL COMPOSITIONS

[75] Inventors: Jacky Mention, Leognan; Rene Tarral, Paris, both of France; Graham S. Leonard, St. Albans, England

[73] Assignee: Laboratories Smith Kline & French, France

[21] Appl. No.: 622,895

[22] Filed: Dec. 5, 1990

[30] Foreign Application Priority Data

Dec. 5, 1989 [FR] France ................ 89 16056

[51] Int. Cl.$^5$ ................................ A61K 9/32
[52] U.S. Cl. .................... 424/482; 424/472; 424/464
[58] Field of Search ............ 424/482, 472, 464

[56] References Cited

U.S. PATENT DOCUMENTS

| | | | |
|---|---|---|---|
| 4,851,228 | 7/1989 | Zentner et al. | 424/456 |
| 4,871,549 | 10/1989 | Ueda et al. | 424/494 |
| 4,940,588 | 7/1990 | Sparks et al. | 424/490 |
| 4,952,402 | 8/1990 | Sparks et al. | 424/419 |
| 4,968,507 | 11/1990 | Zentner et al. | 424/465 |
| 4,976,949 | 12/1990 | Meyer et al. | 424/1.1 |

FOREIGN PATENT DOCUMENTS 313328A 4/1989 European Pat. Off. .
WO88/03794 6/1988 World Int. Prop. O. .

OTHER PUBLICATIONS

Conte, et al., *Il. Farmaco*, vol. 39, No. 3, Mar. 1984.
Ortega et al., *Current Therapeutic Research* 28(5): 692-697 (1980).
Conti et al., *Folia Med.*, 84(5), 407 (1982)-English translation attached.
Speigl et al., *Sci. Pharm.*, 51, 215-218 (1983)-English translation attached.
Hillebrand, *Wien Me. Wochenschrift*, 135, 191 (1985)--English translation attached.
Maysinger et al., *International Journal of Pharmaceutics*, 17, 129-134 (1983).
Marenco et al., *Panminerva Medica*, 27, pp. 182-187 (1985).

*Primary Examiner*—Thurman K. Page
*Assistant Examiner*—W. Benston
*Attorney, Agent, or Firm*—Dara L. Dinner; Stephen Venetianer; Edward T. Lentz

[57] ABSTRACT

Delayed-release oral dosage forms are described comprising cimetidine or a salt thereof and optionally a buffer that is capable of aiding dissolution of cimetidine in the intestine, coated with a release-delaying substance comprising a coating agent such as Eudragit ® L 30 D.

35 Claims, No Drawings

PHARMACEUTICAL COMPOSITIONS

This invention relates to solid pharmaceutical compositions containing cimetidine and methods for their preparation.

Cimetidine is a histamine $H_2$-antagonist which has been described in U.K. Patent Specification 1,397,436. Cimetidine has been shown to be useful in the treatment of duodenal, gastric, recurrent and stomal ulceration, and reflux oesophagitis and in the management of patients who are at high risk from haemorrhage of the upper gastrointestinal tract.

Cimetidine has been made available to patients in a variety of dosage forms; for example tablets, granules, syrups and suspensions. In most, if not all, of these dosage forms, the cimetidine is in an immediate-release form; that is to say the nature of the formulation is such that by the time the cimetidine leaves the stomach, it is either in solution or is in the form of a suspension of fine particles, i.e. a form from which it can be readily absorbed.

Coating agents which prevent release of an active ingredient in the stomach but which allow release in the intestines are known as enteric coating agents and many such substances are known in the art for this purpose. However, it has been found that, when many such release-delaying substances are used in conjunction with cimetidine, although release is delayed, the bioavailability of the cimetidine is substantially reduced In order to test the bioavailability of a given formulation, it is generally necessary to conduct the tests in human volunteers or animals and such tests are thus both time consuming and expensive. In order to provide a cheaper and more convenient means of testing bioavailability, in vitro tests have now been developed. These tests can predict accurately good bioavailability of delayed-release forms of cimetidine. The requirements for these tests have been determined from extensive human bioavailability studies.

In a first aspect, the present invention provides a delayed-release oral dosage form comprising cimetidine or a pharmaceutically acceptable acid addition salt thereof, coated with a release-delaying substance which does not permit more than 10% release of cimetidine after 2 hours in 0.1N hydrochloric acid and which satisfies each of the following dissolution tests (a) to (c) in a European Pharmacopoeia apparatus, with rotating paddle, 100 revolutions per minute, at 37° C. with 800 ml of buffered aqueous dissolution medium comprising sodium hydroxide and 0.04 moles of monopotassium phosphate:

| TEST | Conditions After 2 hours in 0.1N hydrochloric acid and a further time in dissolution medium at pH 5.7, 6.0 or 6.8 | % Release of Cimetidine Formulae with Cimetidine base | Formulae with a pharmaceutically acceptable acid addition salt of cimetidine. |
|---|---|---|---|
| (a) | 5.7 | Minimum 85% after 2 hours | Not applicable |
| (b) | 6.0 | Minimum 75% after 1 hour | Minimum 75% after 2 hours |
| (c) | 6.8 | Minimum 90% after 45 mins. | Minimum 80% after 45 mins. |

For dosage forms comprising a pharmaceutically acceptable acid addition salt of cimetidine it has been found to be unnecessary to conduct test (a) in order to predict good bioavailability. Accordingly, the expression "not applicable" has been inserted into the right hand column of test (a) in the above-noted table.

The dosage forms of this invention can be used to extend the duration of action of cimetidine as well as maintaining good bioavailability with plasma levels greater than the therapeutically effective concentration of 0.5 mg/l. Maintaining such plasma levels, which result in substantial suppression of acid secretion, for extended periods of time increases the rate of healing in gastric or duodenal ulceration and is advantageous in disease states such as gastroesophageal reflux disease, dyspepsia or stress ulceration where prolonged control of acid secretion is desirable.

Preferably the dosage forms of this invention also comprise a buffer that is capable of aiding dissolution of cimetidine in the alkaline environment of the intestine.

Thus in a second aspect this invention provides a delayed-release oral dosage form comprising cimetidine or a pharmaceutically acceptable acid addition salt thereof and a buffer that is capable of aiding dissolution of cimetidine in the intestine, coated with a release-delaying substance which does not permit more than 10% release of cimetidine after 2 hours in 0.1N hydrochloric acid and which satisfies each of the following dissolution tests (b) and (c) in a European Pharmacopoeia apparatus, with rotating paddle, 100 revolutions per minute, at 37° C. with 800 ml of buffered aqueous dissolution medium comprising sodium hydroxide and 0.04 moles of monopotassium phosphate:

| TEST | Conditions After 2 hours in 0.1N hydrochloric acid and a further time in dissolution medium at pH 6.0 or 6.8 | % Release of Cimetidine Formulae with cimetidine or a pharmaceutically acceptable acid addition salt thereof and a buffer. |
|---|---|---|
| (b) | 6.0 | Minimum 50% after 2 hours |
| (c) | 6.8 | Minimum 85% after 1 hour |

The preferred embodiments of this invention which comprise cimetidine together with a buffer give reproducible bioavailability with minimal inter-patient variation.

Suitably the buffer is capable of generating a pH in the range 3.5 to 6 in a 1% aqueous solution, preferably a pH in the range 4 to 4.5, particularly in the range 4 to 4.2

Suitably the dosage forms of this invention comprise a pharmaceutically acceptable addition salt of cimetidine.

Preferably the dosage form of this invention comprises a pharmaceutically acceptable acid addition salt of cimetidine and a buffer that is capable of generating a pH in the range 4.0–4.2 in a 1% aqueous solution, coated with a release delaying substance which does not permit more than 10% release of cimetidine after 2 hours in 0.1N hydrochloric acid and which satisfies each of the following dissolution tests (b) and (c) in a European Pharmacopoeia apparatus, with rotating paddle, 100 revolutions per minute at 37° C. with 800 ml of buffered aqueous medium comprising sodium hydroxide and 0.04 moles of monopotassium phosphate:

| TEST | Conditions After 2 hours in 0.1N hydrochloric acid and a further time in dissolution medium at pH 6.0 or 6.8 | % Release of Cimetidine Formulae with a pharmaceutically acceptable acid addition salt of cimetidine and a buffer. |
| --- | --- | --- |
| (b) | 6.0 | Minimum 60% after 2 hours |
| (c) | 6.8 | Minimum 90% after 1 hour |

The particular dosage forms of the present invention can be any of the commonly used types of solid dosage form. Thus, for example, they can be coated tablets, capsules or granules.

Examples of buffers that can be used in this invention include those formed from citric, tartaric, benzoic and sorbic acids, alkali metal salts thereof, alkali metal phosphates and mixtures thereof. A suitable buffer comprises a mixture of monosodium citrate and disodium citrate.

Suitably the amount of buffer relative to cimetidine should be as much as possible to aid dissolution of cimetidine in the intestine. For a tablet or capsule the maximum amount will be dictated by the size of the unit dosage form which must not be too large to hinder oral administration. Suitably the amount of buffer is between 0.01 to 5 moles per mole of cimetidine, preferably between 0.1 to 0.5 moles per mole of cimetidine.

Examples of acid addition salts of cimetidine include those formed with hydrochloric, hydrobromic, sulphuric, phosphoric, acetic, citric, maleic, lactic, ascorbic, fumaric, oxalic, methanesulphonic and ethane sulphonic acids. Cimetidine hydrochloride is preferred.

In addition to cimetidine or a pharmaceutically acceptable acid addition salt and optionally a buffer, the delayed-release dosage form suitably comprises a pharmaceutically acceptable carrier formulation. Examples of excipients for such carriers include starch, celluloses, lactose, sucrose, magnesium stearate, polyvinylpyrrolidone and sodium laurylsulphate.

Suitably the release-delaying substance comprises a coating agent selected from methacrylic acid copolymers, polymeric methacrylates such as Eudragit ® L, E, S, RL, RS, L 30 D, NE 30 D, RL 30 D, RS 30 D or mixtures thereof, hydroxypropyl methylcellulose phthalate, cellulose acetate phthalate, ethyl cellulose or polyvinyl acetate phthalate, or mixtures thereof.

As well as the above-noted coating agents the release-delaying substance suitably comprises other coating additives well known in the coating art such as:

plasticisers, e.g. acetylated monoglycerides, diethyl phthalate, triacetin, citric esters such as triethyl citrate, acetyl triethyl citrate, tributylcitrate or acetyl tributyl citrate, propylene glycol, tributyrine, butylphthalylbutyl glycolate, glycerine, polyethylene glycols, glyceryl triacetate, dibutyl sebacate, dibutyl phthalate, castor oil or acetyl monoglyceride, lubricants, e.g. calcium stearate, colloidal silicon dioxide, mineral oil, magnesium stearate, polyethylene glycol or talc;

stabilizers and emulsifying agents, e.g. calcium stearate, glyceryl monostearate, hydroxypropyl cellulose, hydroxypropyl methyl cellulose, polysorbate, propylene glycol, carboxymethylcellulose, dextrin, cetostearyl alcohol, mineral oil and lanolin alcohols, polyoxyethylene alkyl ethers, polyoxyethylene castor oil derivatives, polyoxyethylene sorbitan fatty acid esters, polyoxyethylene stearate or sorbitan esters, film disintegrating agents, e.g. lactose, saccharose, starch, cellulose, kaolin, polyvinyl alcohol or hydroxypropyl methyl cellulose; or colouring agents.

The particular amounts of coating agent and coating additives used for the release-delaying substance are variable within limits that can be determined by a skilled worker using the in vitro dissolution tests as hereinbefore defined.

Suitably the release-delaying substance comprises:

| | % (w) |
| --- | --- |
| Coating agent | 40 to 100 |
| Plasticiser | 0 to 20 |
| Lubricant | 0 to 40 |
| Film disintegrating agent | 0 to 40 |

Preferably the coating agent used is Eudragit ® L 30 D. Alternatively, a mixture of Eudragit ® L 30 D and up to 25% of Eudragit ® NE 30 D is used.

Eudragit ® L 30 D is an aqueous dispersion containing 30% (w/w) of an acrylic resin formed from a copolymer based on polymethacrylic acid and acrylic acid esters. The acrylic resin is soluble in intestinal juice from pH 5.5 upwards.

Eudragit ® NE 30 D is an aqueous dispersion containing 30% (w/w) of a neutral copolymer based on ethyl acrylate and methyl methacrylate.

A preferred plasticiser is triethyl citrate and a preferred lubricant is talc.

When the coating agent used comprises a mixture of Eudragit ® NE 30 D and Eudragit ® L 30 D preferably an emulsifying agent such as polysorbate is also present.

When Eudragit ® L 30 D is used as the coating agent, suitably the release-delaying substance is present in an amount of approximately 2 to 30% (w/w) relative to the uncoated dosage form, preferably 2 to 14% (w/w).

In another aspect the present invention provides a delayed-release oral dosage form comprising cimetidine or a pharmaceutically acceptable acid addition salt thereof and optionally a buffer that is capable of generating a pH in the range 3.5 to 6 in a 1% aqueous solution, coated with a release-delaying substance in an amount of 2 to 30% (w/w) relative to the uncoated dosage form, the release-delaying substance comprising:

| | % (w) |
| --- | --- |
| Coating agent | 40 to 100 |
| Plasticiser | 0 to 20 |
| Lubricant | 0 to 40 |
| Film disintegrating agent | 0 to 40 |

For particulate dosage forms such as pellets or granules preferably the release-delaying substance is present in an amount of 10 to 30% (w/w) relative to the uncoated dosage form. For larger dosage forms such as tablets preferably the release delaying substance is present in an amount of 2–20% (w/w) relative to the uncoated dosage form.

Examples of coating agents, plasticisers, lubricants and film disintegrating agents are as hereinbefore described. Particular examples of coating agents include Eudragit ® L or L30D, hydroxypropyl methyl cellulose phthalate, cellulose acetate phthalate or polyvinyl acetate phthalate or mixtures thereof.

A preferred coating agent is a copolymer of polymethacrylic acid and acrylic acid esters that is soluble in intestinal juice from pH 5.5 upwards such as Eudragit ® L30D.

Preferably the cimetidine is in the form of its hydrochloride.

Preferably the buffer is capable of generating a pH of 4 to 4.2 in a 1% aqueous solution.

Suitably the buffer comprises a mixture of monosodium citrate and disodium citrate.

In a further aspect of the invention, there is provided a multi-phase medicament comprising an immediate-release phase containing cimetidine or a pharmaceutically acceptable salt thereof, and at least one delayed-release phase comprising a composition as described above.

For example a suitable medicament can comprise an immediate-release phase to provide a first pulse of cimetidine, a first delayed-release phase to provide a second pulse of cimetidine and a second delayed release phase having a greater amount of release delaying substance than the first delayed-release phase to provide a third pulse of cimetidine. In this manner the duration of action of cimetidine can be extended whilst maintaining good bioavailability. Alternatively the first delayed-release phase may contain a polymer which is soluble from pH 5.5 upwards (e.g. Eudragit ® L30D) and the second delayed-release phase may contain a polymer which is soluble from pH 6 upwards (e.g. Eudragit ® L). Due to the different solubilities of the polymers the first delayed-release phase will release cimetidine sooner than the second delayed phase in the intestinal tract.

The immediate and delayed-release phases can be presented separately or combined in a single dosage form. Thus, for example, a combination can take the form of a bilayer tablet or a layered tablet in which the immediate-release phase is compressed or coated around a delayed-release core. Alternatively, the immediate-release and delayed-release phases can take the form of uncoated and coated tablets or pellets contained within a gelatine capsule.

The immediate-release phase typically will comprise uncoated cimetidine, or cimetidine particles which are coated by a coating agent which dissolves in the gastric juices. Preferably the cimetidine is in the form of an acid addition salt as hereinbefore described. Preferably the immediate-release phase comprises a disintegrating agent such as starch, cellulose, sodium croscarmellose, sodium starch glycolate, crospovidone, kaolin, polyvinyl alcohol or low viscosity hydroxypropyl methyl celluloses.

Suitably the delayed-release cimetidine and the immediate-release cimetidine are administered in a ratio 5:1 to 1:1, suitably 3:1 to 1:1, preferably in a ratio of 5:3, calculated as the free base of cimetidine. Thus, for a single 800 mg dose of cimetidine it is possible to administer 2 delayed-release cimetidine tablets (each containing 250 mg of cimetidine hydrochloride calculated as the free base) and 2 immediate-release cimetidine tablets (each containing 150 mg of cimetidine hydrochloride calculated as the free base). More conveniently a single dosage form comprises 250 mg of delayed-release cimetidine hydrochloride surrounded by 150 mg of immediate-release cimetidine hydrochloride, both calculated as the free base. Other embodiments include a capsule containing a tablet of immediate-release cimetidine (300 mg) and a tablet of delayed-release cimetidine (300 mg) or a capsule containing uncoated pellets of cimetidine (60 mg) and coated pellets of cimetidine (240 mg).

In another aspect of the invention, there is provided a medicament comprising a delayed-release phase containing cimetidine as hereinbefore defined and a further therapeutic agent which is in a form which enables it to be released in the stomach.

The further therapeutic agent can be, for example, an antacid such as magnesium hydroxide or an alkali metal or alkaline earth metal carbonate or bicarbonate or a stomach mucosa protective agent such as sucralfate.

The cimetidine phase and the phase containing the other therapeutic agent can be presented as separate entities or combined in a single dosage form in a manner analogous to that described above for the immediate-release delayed-release multi-phase cimetidine medicaments.

In a preferred embodiment, the medicament comprises a sucralfate layer compressed around a cimetidine-containing coated core.

The invention will now be illustrated by means of the following description, bioavailability study results and examples.

Description—In Vitro Dissolution Tests

Apparatus

All parts of the apparatus which come into contact with the sample or with the dissolving medium must be chemically inert and must neither adsorb the substance to be examined nor react in its presence, nor affect its behaviour.

No part of the apparatus nor the assembly in which it is situated should exert any significant movement of stirring or of vibration other than those of the low-speed rotating element.

The dissolution apparatus, called a paddle apparatus, consists of a cylindrical vessel, a stirrer and a thermostatted bath.

The hemispherical-bottomed cylindrical vessel, of nominal capacity 1000 ml, is made of borosilicate glass or another appropriate transparent material. The vessel is fitted with a lid to prevent evaporation and having a central aperture for the stirrer shaft and also several other apertures allowing a thermometer and sampling devices to be introduced.

The stirrer consists of a vertical shaft to the lower part of which is attached a paddle whose shape corresponds to that of the portion of a circle bounded by two parallel planes. The paddle is inserted into the centre of the shaft in such a way that its base is at exactly the level of the end of the shaft. The shaft is positioned so that its axis is not more than 2 mm from that of the vessel and the lower part of the paddle is situated at a distance of 25±2 mm from the bottom of the vessel. The upper part of the shaft of the stirrer is connected to a motor equipped with a speed regulator. The rotation of the stirrer must be uniform, without significant oscillation.

The thermostatted bath in which the vessel is immersed must allow the temperature of the solution medium to be maintained at 37°±0.5° C. during the test.

Reagents 0.1N Hydrochloric acid pH 5.7 buffer: To 250 ml of 0.2 M monopotassium phosphate solution (27.22 g of $KH_2PO_4$ per liter) add 735 ml of purified water, adjust the pH to 5.7±0.05 by means of a 0.2N solution of sodium hydroxide (about 20 ml). Make up to 1000 ml with purified water. Mix.

pH 6.0 buffer: To 250 ml of 0.2M monopotassium phosphate solution (27.22 g of $KH_2PO_4$ per liter) add 715 ml of purified water, adjust the pH to 6±0.05 by means of a 0.2N solution of sodium hydroxide (about 31 ml). Make up to 1000 ml with purified water. Mix.

pH 6.8 buffer: To 250 ml of 0.2M monopotassium phosphate solution (27.22 g of $KH_2PO_4$ per liter) add 620 ml of purified water, adjust the pH to 6.8±0.05 by means of a 0.2N solution of sodium hydroxide (about 125 ml). Make up to 1000 ml with purified water. Mix.

Procedure

Standard Solution

Introduce an exactly weighed test amount $P_s$ of about 79 mg of standard reference cimetidine into a 500 ml volumetric flask. Dissolve and make up to 500 ml with the buffer under study (buffer of pH 5.7, 6.0 or 6.8). Mix.

Dilute this solution to exactly one 5th with 0.1N hydrochloric acid.

Operating Procedure

Introduce 800 ml of the dissolving medium into the vessel. Assemble the apparatus. Warm the dissolving medium to 37°±0.5° C. and withdraw the thermometer.

Place the product at the bottom of the vessel before the paddle is set in motion.

When placing the product under study in the apparatus, take care to avoid the formation of bubbles on the surface of the sample and immediately set the apparatus in motion at the speed of 100 RPM, controlled to a precision of ±4 percent. Every 15 minutes, take a sample (5 ml) in a region halfway between the surface of the liquid and the top of the paddle and at least 10 mm from the wall of the vessel.

Compensate the amount removed for calculations.

Filter the samples at 37° C. and carry out a dilution to one 5th in 0.1N hydrochloric acid.

Read the absorbance of each dilution in a 1 cm cuvette at 218 nm and at 260 nm, taking a dilution of the buffer studied to one 5th in 0.1N hydrochloric acid as the compensation liquid.

Read the absorbance of the standard solution under the same conditions.

For the standard solution and each dilution prepared from each of the samplings, calculate:

$$\Delta(OD) = OD_{218\,nm} - OD_{260\,nm}$$

From the $\Delta(OD)$ value found for the standard solution, the value $P_s$ and the $\Delta(OD)$ values obtained for each sampling, calculate the percentage of the active principle dissolved at each time, allowing for the quantities sampled for the measurement.

Results

The tablets of Examples 1 and 2 gave 0% dissolution after 2 hours in 0.1N hydrochloric acid and satisfied each of the tests (a) to (c) as follows:

| TEST | Conditions After 2 hours in 0.1N hydrochloric acid and a further time in dissolution medium at pH 5.7, 6.0 or 6.8 | % Release of Cimetidine Formulae with Cimetidine base | |
|---|---|---|---|
| | | Example 1 | Example 2 |
| (a) | 5.7 | 100 after 2 hours | 100 after 2 hours |
| (b) | 6.0 | 91 after 1 hour | 100 after 1 hour |
| (c) | 6.8 | 95 after 45 mins. | 100 after 45 mins. |

The tablets of Examples 3 to 6 gave 0% dissolution after 2 hours in 0.1N hydrochloric acid and satisfied each of the tests (b) and (c) as follows:

| TEST | Conditions After 2 hours in 0.1N hydrochloric acid and a further time in dissolution medium at pH 6.0 or 6.8 | % Release of Cimetidine Formulae with Cimetidine Hydrochloride | | | |
|---|---|---|---|---|---|
| | | Ex 3 | Ex 4 | Ex 5 | Ex 6 |
| (b) | 6.0 | 100 after 2 hrs | 100 after 2 hrs | 95.5 after 2 hrs | 100 after 2 hrs |
| (c) | 6.8 | 100 after 45 mins. | 100 after 45 mins. | 99.5 after 45 mins. | 91.4 after 45 mins. |

The tablets of Examples 7 to 9 gave 0% release of cimetidine after 2 hours in 0.1N hydrochloric acid and satisfied each of the tests (b) and (c) as follows:

| TEST | Conditions After 2 hours in 0.1N hydrochloric acid and a further time in dissolution medium at pH 6.0 or 6.8 | % Release of Cimetidine Formulae with Cimetidine Hydrochloride & buffer | | |
|---|---|---|---|---|
| | | Ex 7 | Ex 8 | Ex 9 |
| (b) | 6.0 | 100 after 2 hours | 66.8 after 2 hours | 81.0 after 2 hours |
| (c) | 6.8 | 100 after 1 hour | 100 after 1 hour | 97.1 after 1 hour |

Bioavailability Study Results

The following treatments were used to assess the bioavailability of the formulations of the present invention:

Treatment A': Two 110 mg tablets of Example 1
Treatment B': Two 110 mg tablets of Example 2
Treatment C': Two 110 mg tablets of Example 3
Treatment D': One 200 mg Tagamet ® tablet (immediate-release).
Treatment A: Two 250 mg tablets of Example 4 + two 1 150 mg tablets of Example 10.
Treatment B: Two 250 mg tablets of Example 8 + two 150 mg tablets of Example 10
Treatment C: Two 250 mg tablets of Example 7 + two 150 mg tablets of Example 10.
Treatment D: Two 250 mg tablets of Example 6 + two 150 mg tablets of Example 10.
Treatment E: Two 250 mg tablets of Example 5 + two 150 mg tablets of Example 10.

Treatment F: Two 250 mg tablets of Example 9+two 150 mg tablets of Example 10.

Treatment G: One 800 mg Tagamet ® tablet (immediate-release).

A first group of three patients each received a 220 mg dose of cimetidine according to treatments A', B' and C'. One patient within this group also received subsequently a 200 mg dose of cimetidine according to treatment D'.

A second group of three patients each received an 800 mg dose of cimetidine according to treatments A, C, E and G. A third group of three patients each received an 800 mg dose of cimetidine according to treatments B, D, F and G. At least seven days elapsed between each treatment. Blood plasma levels were monitored from which the following parameters were determined:

$T_{max}$ (hours): Time to reach maximum plasma concentration $C_{max}$ (mg/l): Maximum plasma concentration T0.5 (hours): Time during which plasma concentration is greater than 0.5 mg/l AUC (mg/h/l): Area under plasma concentration against time curve.

The following results were obtained

| Treatment | Group 1 | | | |
|---|---|---|---|---|
| | A' | B' | C' | D' |
| $T_{max}$ | 3.66 | 3.02 | 2.28 | 0.75 |
| $C_{max}$ | 0.71 | 0.86 | 1.25 | 1.06 |
| $T_{0.5}$ | 1.86 | 1.90 | 2.23 | 1.50 |
| AUC | 2.86 | 2.93 | 3.30 | 2.64 |

| Treatment | Group 2 | | | |
|---|---|---|---|---|
| | A | C | E | G |
| $T_{max}$ | 3.44 (0.42) | 4.55 (0.63) | 3.58 (0.58) | 1.75 (0.74) |
| $C_{max}$ | 4.71 (0.74) | 3.27 (0.26) | 4.12 (0.55) | 3.83 (0.81) |
| $T_{0.5}$ | 8.48 (0.22) | 8.93 (0.16) | 8.31 (1.00) | 6.74 (0.89) |
| AUC | 17.06 (2.35) | 14.36 (0.39) | 15.33 (1.65) | 14.17 (1.63) |

| Treatment | Group 3 | | | |
|---|---|---|---|---|
| | B | D | F | G |
| $T_{max}$ | 5.00 (0.00) | 4.50 (0.41) | 4.33 (0.94) | 1.33 (0.31) |
| $C_{max}$ | 3.05 (1.12) | 3.18 (0.54) | 3.24 (1.15) | 4.81 (0.90) |
| $T_{0.5}$ | 9.17 (1.11) | 9.21 (0.08) | 9.81 (1.09) | 8.09 (0.67) |
| AUC | 14.76 (4.02) | 14.61 (1.47) | 15.38 (3.15) | 17.51 (1.82) |

Figures in parenthesis represent standard deviations.

A direct comparison of the results in Group 1 cannot be made since treatments A', B' and C' used 10% more cimetidine than treatment D, However, it is still evident that the tablets of Examples 1 to 3 exhibit delayed-release characteristics ($T_{max}$ has been extended) whilst maintaining adequate bioavailability (as demonstrated by $T_{0.5}$ and AUC).

Comparing the results of treatments A, C, E and G in group 2 it is evident that treatment using compositions of the present invention prolong the duration of action by about 1.6 to 2.2 hours (as measured by $T_{0.5}$) and increase the bioavailability (as measured by AUC). Although results in Group 3 indicate that the bioavailability following treatment B, D or F is less than that following treatment G, the time during which plasma concentrations are greater than the therapeutically effective level of 0.5 mg/l is extended by more than one hour.

EXAMPLE 1

Delayed-release (Cimetidine free base/Eudragit L 30 D and NE 30 D Coating

| Ingredients | mg./tablet |
|---|---|
| Cimetidine | 110.000 |
| Corn Starch | 3.685 |
| Microcrystalline cellulose | 0.887 |
| Sodium starch glycolate | 4.443 |
| Polyvinylpyrrolidone | 3.685 |
| Sodium laurylsulphate | 0.275 |
| Magnesium stearate | 0.670 |

Half of the polyvinylpyrrolidone was dissolved in purified water to give a 9% w/v solution. The sodium laurylsulphate was dissolved in this solution. The cimetidine, starch and the remainder of the polyvinylpyrrolidone were introduced into a fluidised bed granulator and granulated with the above solution. The wet granulation was dried, to give a residual moisture content of 2.2% (w/w), and then screened through a 1.2 mm mesh screen. The remaining excipients were added and mixed and the mixture was compressed into a tablet core.

The tablet cores were each coated with a coating suspension having the following composition:

| Ingredients | % w/w |
|---|---|
| Eudragit N E 30 D | 6.67 |
| Eudragit L 30 D | 20.00 |
| Polysorbate 80 | 0.40 |
| Talc | 4.00 |
| Triethyl citrate | 0.90 |
| Purified Water | 68.03 |

The tablet cores were coated using a Uniglatt fluidised bed apparatus fitted with a six inch Wurster bottom spray apparatus. The operating conditions were as follows:

| Charge | 400 g. of tablets |
|---|---|
| Temperature at the entry | 60–65° C. |
| Air intake valve | Position 30 |
| Pipe | 1 mm |
| Spraying pressure | 2.1–2.2 bars |
| Core pre-heating | air outlet 34° C. |
| Flow | 8.6 g/minute |
| Amount of coating suspension sprayed | 500 g |
| Air outlet temperature during process | 34–36° C. |

At the end of the operation, the tablets were dried in an open air oven for one night.

| Quantity of coated tablets recovered | 440.6 g |
|---|---|
| Average weight of coated tablet | 136.09 mg |
| Average weight of tablet core | 123.26 mg |
| Approximate weight of tablet coating | 12.83 mg |
| Average thickness of coated tablet | 4.52 mm |
| Average thickness of tablet core | 4.29 mm |
| Approximate thickness of tablet coating | 0.115 mm. |
| % weight of coating relative to tablet core | 10.4 |

EXAMPLE 2

Delayed-release (Cimetidine free base/Eudragit L 30 D Coating)

Tablet cores as prepared in Example 1 were each coated with a coating suspension having the following composition:

| Ingredients | % (w.w) |
|---|---|
| Eudragit L 30 D | 26.64 |
| Talc | 4.00 |
| Triethylcitrate | 1.20 |
| Purified Water | 68.16 |

The coating procedure and coating conditions were substantially as described in Example 1 except that, for 400 g of tablet cores, 400.4 g of coating suspension was used.

| | |
|---|---|
| Average weight of coated tablet | 136.01 mg |
| Average weight of tablet core | 123.27 mg |
| Approximate weight of tablet coating | 12.74 mg |
| Average thickness of coated tablet | 4.58 mm |
| Average thickness of tablet core | 4.40 mm |
| Approximate thickness of tablet coating | 0.09 mm. |
| % weight of coating relative to tablet core | 10.3 |

EXAMPLE 3

Delayed-release (Cimetidine HCl/Eudragit L 30 D Coating)

| Ingredients | mg./tablet |
|---|---|
| Cimetidine base in the form of its hydrochloride | 110.000* |
| Corn Starch | 3.685 |
| Microcrystalline cellulose | 0.887 |
| Sodium starch glycolate | 4.443 |
| Polyvinylpyrrolidone | 3.685 |
| Sodium laurylsulphate | 0.275 |
| Magnesium stearate | 0.670 |

*corresponding to 133.76 mg of cimetidine hydrochloride monohydrate.

Half of the polyvinylpyrrolidone was dissolved in purified water to give a 9% w/v solution. The sodium laurylsulphate was dissolved in this solution. The cimetidine, starch and the remainder of the polyvinylpyrrolidone were mixed, moistened with the above solution and, if necessary, with further purified water and then granulated through a 3.15 mm mesh grid. The wet granulation was dried in a fluidised bed dryer, to give a residual moisture content of 5.0% (w/w), and then screened through a 1.25 mm mesh screen. The remaining excipients were added and mixed and the mixture was compressed into a tablet core.

The tablet cores were each coated with a coating suspension having the same composition as described in Example 2.

The coating procedure and coating conditions were substantially as described in Example 1, except that, for 400 g of tablet cores, 250.25 g of coating suspension was used.

| | |
|---|---|
| Average weight of coated tablet | 154.78 mg |
| Average weight of tablet core | 146.67 mg |
| Approximate weight of tablet coating | 8.11 mg |
| Average thickness of coated tablet | 4.42 mm |
| Average thickness of tablet core | 4.29 mm |
| Approximate thickness of tablet coating | 0.065 mm. |
| % weight of coating relative to tablet core | 5.5 |

EXAMPLE 4

Delayed-release (Cimetidine HCl/Eudragit L 30 D Coating)

| Ingredients | mg./tablet |
|---|---|
| Cimetidine base in the form of its hydrochloride | 250.000* |
| Corn Starch | 8.374 |
| Microcrystalline cellulose | 2.016 |
| Sodium starch glycolate | 10.101 |
| Polyvinylpyrrolidone | 8.374 |
| Sodium laurylsulphate | 0.624 |
| Magnesium stearate | 2.380 |

*corresponding to 304 mg of cimetidine hydrochloride monohydrate.

Half of the polyvinylpyrrolidone was dissolved in purified water to give a 9% w/v solution. The sodium laurylsulphate was dissolved in this solution. The cimetidine, starch and the remainder of the polyvinylpyrrolidone were mixed, moistened with the above solution and, if necessary, with further purified water and then granulated through a 2.5 mm mesh grid. The wet granulation was dried in a fluidised bed dryer, to give a residual moisture content of 5.6% (w/w), and then screened through a 1 mm mesh screen. The remaining excipients were added and mixed and the mixture was compressed into a tablet core.

The tablet cores were each coated with a coating suspension having the same composition as described in Example 2.

The tablet cores were coated using a Erweka coating turbine, a Master drying gun and a Uniglatt coating gun. The operating conditions for 400 g of tablet cores are as follows:

Pre-heating

| | |
|---|---|
| turbine speed | 5 revs/min. |
| air temperature | 60° C. |
| temperature of tablets | 32° C. |
| pre-heating time | 5 minutes. |

Coating

| | |
|---|---|
| distance from nozzle to tablet bed | 13 cm |
| flow | 7 g/min |
| spraying pressure | 0.5 bars |
| turbine speed | 16 revs/min. |
| air temperature | 60° C. |
| temperature of tablets | 26-28° C. |
| process time | 65 minutes |
| quantity of coating suspension sprayed | 413 g |

| | |
|---|---|
| Average weight of coated tablet | 350.75 mg |
| Average weight of tablet core | 336.20 mg |
| Approximate weight of tablet coating | 14.55 mg |
| Average thickness of coated tablet | 5.22 mm |
| Average thickness of tablet core | 5.13 mm |
| Approximate thickness of tablet coating | 0.045 mm |

| | |
|---|---|
| % weight of coating relative to tablet core | 4.32. |

EXAMPLE 5

Delayed-release (Cimetidine HCl/Eudragit L 30 D Coating)

Tablet cores as prepared in Example 4 were each coated with a coating suspension having the same composition as described in Example 2. The coating procedure and coating conditions were substantially as described in Example 4 except that, for 500 g of tablet cores, 1001 g of coating suspension was used.

| | |
|---|---|
| Average weight of coated tablet | 374.10 mg |
| Average weight of tablet core | 336.20 mg |
| Approximate weight of tablet coating | 37.90 mg |
| Average thickness of coated tablet | 5.34 mm |
| Average thickness of tablet core | 5.13 mm |
| Approximate thickness of tablet coating | 0.105 mm. |
| % weight of coating relative to tablet core | 11.3. |

EXAMPLE 6

Delayed-release (Cimetidine HCl/Eudragit L 30 D and NE 30 D Coating)

Tablet cores as prepared in Example 4 were each coated with a coating suspension having the same composition as described in Example 1.

The coating procedure and coating conditions were substantially as described in Example 4, except that for 500 g of tablet cores, 937.7 g of coating suspension was used.

| | |
|---|---|
| Average weight of coated tablet | 368.55 mg |
| Average weight of tablet core | 336.20 mg |
| Approximate weight of tablet coating | 32.35 mg |
| Average thickness of coated tablet | 5.30 mm |
| Average thickness of tablet core | 5.13 mm |
| Approximate thickness of tablet coating | 0.085 mm. |
| % weight of coating relative to tablet core | 9.6. |

EXAMPLE 7

Delayed-release (Cimetidine HCl+Citrate buffer/Eudragit L 30 D Coating)

| Ingredients | mg./tablet |
|---|---|
| Cimetidine base in the form of its hydrochloride | 250.000* |
| Corn Starch | 8.374 |
| Microcrystalline cellulose | 2.016 |
| Sodium starch glycolate | 10.101 |
| Polyvinylpyrrolidone | 8.374 |
| Sodium laurylsulphate | 0.624 |
| Magnesium stearate | 2.380 |
| Monosodium citrate | 56.958 |
| Disodium citrate 1.5 H$_2$O | 27.760 |

*corresponding to 304 mg of cimetidine hydrochloride monohydrate.

Half of the polyvinylpyrrolidone was dissolved in purified water to give a 9% w/v solution. The sodium laurylsulphate was dissolved in this solution. The cimetidine, starch, monosodium and disodium citrates and the remainder of the polyvinylpyrrolidone were mixed, moistened with the above solution and, if necessary, with further purified water and then granulated through a 2.5 mm mesh grid. The wet granulation was dried in a fluidised bed dryer, to give a residual moisture content of 5.3% (w/w), and then screened through a 1 mm mesh screen. The remaining excipients were added and mixed and the mixture was compressed into a tablet core.

The tablet cores were each coated with a coating suspension having the same composition as described in Example 2. The coating procedure and coating conditions were substantially as described in Example 4 except that, for 500 g of tablet cores, 750.79 g of coating suspension was used.

| | |
|---|---|
| Average weight of coated tablet | 454.10 mg |
| Average weight of tablet core | 422.70 mg |
| Approximate weight of tablet coating | 31.40 mg |
| Average thickness of coated tablet | 5.54 mm |
| Average thickness of tablet core | 5.39 mm |
| Approximate thickness of tablet coating | 0.075 mm. |
| % weight of coating relative to tablet core | 7.4. |

EXAMPLE 8

Delayed-release (Cimetidine HCl+citrate buffer/Eudragit L 30 D Coating)

Tablet cores as prepared in Example 7 were each coated with a coating suspension having the same composition as described in Example 2. The coating procedure and coating conditions were substantially as described in Example 4 except that, for 500 g of tablet cores, 1001 g of coating suspension was used.

| | |
|---|---|
| Average weight of coated tablet | 467.60 mg |
| Average weight of tablet core | 422.70 mg |
| Approximate weight of tablet coating | 44.90 mg |
| Average thickness of coated tablet | 5.60 mm |
| Average thickness of tablet core | 5.39 mm |
| Approximate thickness of tablet coating | 0.105 mm. |
| % weight of coating relative to tablet core | 10.6. |

EXAMPLE 9

Delayed-release (Cimetidine HCl+Citrate Buffer/Eudragit L 30 D and NE 30 D Coating)

Tablet cores as prepared in Example 7 were each coated with a coating suspension having the same composition as described in Example 1. The coating procedure and coating conditions were substantially as described in Example 4 except that, for 500 g of tablet cores, 937.7 g of Eudragit coating suspension was used.

| | |
|---|---|
| Average weight of coated tablet | 479.40 mg |
| Average weight of tablet core | 422.70 mg |
| Approximate weight of tablet coating | 56.70 mg |
| Average thickness of coated tablet | 5.66 mm |
| Average thickness of tablet core | 5.39 mm |
| Approximate thickness of tablet coating | 0.135 mm. |
| % weight of coating relative to tablet core | 13.4. |

EXAMPLE 10

Immediate-release phase (Cimetidine hydrochloride)

| Ingredients | mg./tablet |
|---|---|
| Cimetidine base in the form of its hydrochloride | 150.000* |

| Ingredients | mg./tablet |
|---|---|
| Corn Starch | 9.000 |
| Microcrystalline cellulose | 98.000 |
| Sodium starch glycolate | 12.000 |
| Polyvinylpyrrolidone | 9.000 |
| Sodium laurylsulphate | 0.600 |
| Magnesium stearate | 3.144 |
| Lactose (fast flow) | 35.714 |
| Lactose (Codex) | 99.286 |

*corresponding to 182.4 mg of cimetidine hydrochloride monohydrate.

Half of the polyvinylpyrrolidone was dissolved in purified water to give a 9% w/v solution. The sodium laurylsulphate was dissolved in this solution. The cimetidine, starch, lactose and the remainder of the polyvinylpyrrolidone were mixed, moistened with the above solution and, if necessary, with further purified water and then granulated through a 2.5 mm mesh grid. The wet granulation was dried in a fluidised bed dryer, to give a residual moisture content of 3.0% (w/w), and then screened through a 1.25 mm mesh screen. The remaining excipients were added and mixed and the mixture was compressed into a tablet core.

EXAMPLE 11

Delayed-release/Immediate-release tablets

An immediate-release phase of cimetidine hydrochloride was prepared as described in Example 10 and was compressed around the delayed-release phase tablets prepared as in Example 7. Tablets comprising 250 mg of delayed-release cimetidine (in the form of its hydrochloride) and 150 mg of immediate-release cimetidine (in the form of its hydrochloride) were thereby obtained.

EXAMPLE 12

Delayed-release/Immediate-release tablets

Delayed-release tablets as prepared in Example 7 were each coated with a coating solution having the following composition:

|  | % (w/w) |
|---|---|
| Cimetidine hydrochloride | 15.796 |
| Hydroxypropyl methylcellulose 15 cp | 1.380 |
| Hydroxypropyl methylcellulose 5 cp | 3.220 |
| Propylene glycol | 0.460 |
| Purified Water | 79.144 |

Tablets were coated using a Erweka coating turbine, a master drying gun and a Uniglatt coating gun. The operating conditions for 500 g of tablets are as follows:

Pre-heating

| turbine speed | 5 revs/min |
|---|---|
| air temperature | 75° C. |
| temperature of tablets | 38° C. |
| pre-heating time | 5 min. |

Coating

| distance from nozzle to tablet bled | 12 cm |
|---|---|
| flow | 4 g/min |
| spraying pressure | 0.7 bar |
| turbine speed | 16 revs/min |
| air temperature | 75° C. |
| temperature of tablets | 38° C. |
| process time | 5 h 10 min |
| quantity of coating solution sprayed | 1232 g |
| Average weight of tablets before spraying | 454.10 mg |
| Average weight of tablets after spraying with immediate-release phase | 682 mg |
| Approximate weight of immediate-release coating | 227.9 mg. |

The above coating conditions result in tablets wherein the intermediate-release phase has the following composition:

|  | mg/tablet |
|---|---|
| Cimetidine base in the form of its hydrochloride | 150.000* |
| Hydroxypropyl methylcellulose 15 cp | 15.000 |
| Hydroxypropyl methylcellulose 5 cp | 35.000 |
| Propylene glycol | 5.000 |

*corresponding to 171.675 mg of anhydrous cimetidine hydrochloride.

EXAMPLE 13

Cimetidine/Sucralfate Tablet

This is prepared by compressing a sucralfate immediate-release phase around the delayed-release cimetidine tablets of Example 7.

Sucralfate Immediate-Release Phase

| Ingredients | Mg./Tablet |
|---|---|
| Sucralfate | 500.00 |
| Polyethyleneglycol 6000 | 15.16 |
| Corn Starch | 90.80 |
| Magnesium Stearate | 3.04 |
|  | 609.00 |

The polyethyleneglycol 6000 is dissolved in sufficient distilled water to make a 3.5% (w/w) solution. The starch and sucralfate are mixed and granulated with the polyethyleneglycol solution. The granulation is screened (2.5 mm mesh screen) and dried. Magnesium stearate is mixed with the dried granules.

The above immediate-release granules are then press-coated around the delayed-release core using a multi-layer rotary tablet machine, to give delayed-release cimetidine/immediate-release sucralfate tablets.

Instead of preparing a single cimetidine/sucralfate tablet, the same dose may be provided by two tablets prepared in analogous manner but each containing half the ingredients of the single dosage form.

EXAMPLE 14

Repeat Action Capsules (Cimetidine Free Base/Eudragit L30D Coating)

One immediate-release (core) and one delayed release (enteric coated) tablet are contained within a hard gelatin capsule.

Core Manufacture

| Ingredients | mg/Tablet |
|---|---|
| Cimetidine | 300.00 |
| Corn Starch | 15.00 |
| Microcrystalline Cellulose | 5.00 |

-continued

| Ingredients | mg/Tablet |
| --- | --- |
| Sodium Starch Glycollate | 12.00 |
| Polyvinylpyrrolidone | 12.00 |
| Magnesium Stearate | 3.00 |
| | 347.00 |

The cimetidine, starch, and polyvinylpyrrolidone are introduced into a Pharma Matrix high speed blender/granulator. The powders are mixed together before they are granulated with purified water. The wet granulation is dispensed onto trays and dried in an oven at 60° C. to give a target residual moisture content of 0.8% w/w, within the limits of 0.6–1.0% w/w. The dry granules are then screened through a 12 mesh sieve and blended with the remaining excipients using the cone blender. The mixture is then compressed into 7.5 mm diameter tablet cores with a theoretical weight of 347.0 mg±3%, having an average hardness of 16.1 SC.

Coating

Tablets intended to give delayed-release are coated with a coating suspension having the following composition:

| Ingredients | % w/w |
| --- | --- |
| Eudragit L30D | 53.3 |
| Talc | 1.6 |
| Polyethylene Glycol | 1.6 |
| Antifoam Emulsion | 0.1 |
| Purified Water | 43.4 |

The tablet cores are coated using a twenty-four inch round backed, stainless steel coating pan fitted with a Manesty spray gun and Spraytab unit. The operating conditions are as follows:

| | |
| --- | --- |
| Inlet air temperature | 60° C. (approx) |
| Spray Nozzle details | 1.5 mm needle with 1.8–2.0 mm nozzle |
| Pan Speed | 12 rpm |
| Spraying Pressure | 50 psi |
| Tablet bed temperature | 30–33° C. |
| Process Time | 180 minutes |
| Average weight of coated tablets | 384.3 mg |
| Average weight of tablet cores | 345.4 mg |
| Approximate weight of tablet coat | 38.9 mg |
| % Weight of coat (relative to tablet core) | 11.26 |

Encapsulation

The tablets are encapsulated using a capsule filling machine. The empty gelatin capsules are separated by the machine and using an attached tablet counterfeeder, are filled with one tablet core and one coated tablet. The capsule contents are checked prior to closure.

To keep the dosage size to a minimum, an optimum capsule size and shape is used, e.g. Capsugel's Coni-snap Supro ® Size A.

EXAMPLE 15

Repeat Action Capsules (Cimetidine Free Base/Eudragit L30D Coating)

Uncoated immediate-release cimetidine pellets and enterically-coated cimetidine pellets are contained within a hard gelatin capsule.

Manufacture of Uncoated Pellets

| Ingredients | % w/w |
| --- | --- |
| Cimetidine | 85 |
| Microcrystalline Cellulose | 12 |
| Gelatin | 3 |
| (Water | qs) |

The cimetidine and part of the microcrystalline cellulose are dry blended in a high shear mixer. Mixing is continued while a solution of the gelatin in water is added. When homogenously massed the material is passed through an extruder and recirculated through it once. The extrudate is transferred to a Marumerizer bowl and spheronized. The rest of the microcrystalline cellulose is used as dusting powder to facilitate this stage of the process. The pellets are discharged and spread out on trays to be dried in a hot air oven. The dried pellets are screened between 1.4 mm and 0.6 mm to remove oversize and undersize fractions.

Coating of Pellets

| Composition of coating suspension | % w/w |
| --- | --- |
| Eudragit L30D | 51.2 |
| Triethyl citrate | 2.3 |
| Colloidal silicon dioxide | 1.2 |
| Water | 45.3 |

Pellets obtained as described above are coated by bottom spraying with the coating suspension in Fluidised Bed equipment until a 20% gain in weight is achieved. These coated pellets therefore contain 85/120=70.8% of cimetidine. The coated pellets are dried in situ before discharge, and then allowed to cure overnight at room temperature, while spread out on trays. The approximate weight of a coated pellet is about 0.8 mg.

Encapsulation

Uncoated and coated pellets are filled into capsules such that one capsule contains:

70.6 mg of uncoated pellets comprising 60 mg cimetidine 338.8 mg of coated pellets comprising 240 mg cimetidine Thus two capsules provide a 600 mg dose of cimetidine wherein the ratio of delayed-release to immediate-release cimetidine is 4:1.

Eudragit is a registered trademark of Röhm Pharma Gmbh, Weiterstadt, D-6100 Darmstadt 1, Germany.

What is claimed is:

1. A delayed release oral dosage form comprising cimetidine or a pharmaceutically acceptable acid addition salt thereof coated with a pH dependent release-delaying substance and which in a European Pharmacopoeia apparatus release test with rotating paddle, 100 revolutions per minute, at 37° C. with 800 ml of buffered aqueous dissolution medium comprising sodium hydroxide and 0.04 moles of monopotassium, phosphate satisfies the following separate dissolution tests: (a) does not permit more than 10% release of cimetidine after two hours in 0.1N hydrochloric acid; (b) releases at least 85% of cimetidine after two hours in 0.1N hydrochloric acid, and a further two hours in a dissolution medium of pH 5.7; (c) releases at least 75% cimetidine after 2 hours in 0.1N hydrochloric acid, and a further 1 hour in a dissolution medium at pH 6.0; and, (d) releases at least 90% cimetidine after two hours in 0.1N hydrochloric acid, and a further 45 minutes in a dissolution medium of pH 6.8, and when said dosage form contains the pharmaceutically acceptable acid addition salt (a) less than 10% of cimetidine is released after 2 hours, in 0.1N hydrochloric acid; (b) releases at least 75% cimetidine after 2 hours in 0.1N hydrochloric acid, and a further 2 hours in a dissolution medium of pH 6.0; and, (c) releases at least 80% cimetidine after 2 hours in 0.1N hydrochloric acid, and a further 45 minutes in dissolution medium of pH 6.8.

2. A delayed release oral dosage form comprising cimetidine or a pharmaceutically acceptable acid addition salt thereof, and a buffer that is capable of aiding dissolution of cimetidine in the intestine, coated with a pH dependent release-delaying substance, and which in a European Pharmacopoeia apparatus release test with rotating paddle 100 revolutions per minute at 37° C. and 800 ml of buffered aqueous dissolution medium comprising sodium hydroxide and 0.04 moles of monopotassium phosphate satisfies the following separate dissolution tests: (a does not permit more than 10% release of cimetidine after 2 hours in a 0.1N hydrochloric acid; (b) releases at least 50% cimetidine after 2 hours in 0.1N hydrochloric acid, and a further 2 hours in a dissolution medium of pH 6.0; (c) releases at least 85% cimetidine after 2 hours in 0.1N hydrochloric acid, and a further 1 hour in a dissolution medium of pH 6.8.

3. A dosage form according to claim 2 wherein the buffer is capable of generating a pH in the range 3.5 to 6 in a 1% aqueous solution.

4. A dosage form according to claim 3 which comprises a pharmaceutically acceptable acid addition salt of cimetidine and a buffer that is capable of generating a pH in the range of 4.0–4.2 in a 1% aqueous solution coated with a pH dependent release delaying substance which in a European Pharmacopoeia apparatus release test with rotating paddle, 100 revolutions per minute at 37° C. with 800 ml of buffered aqueous medium comprising sodium hydroxide and 0.04 moles of potassium phosphate satisfies the following separate dissolution tests: (a) does not permit more than 10% release of cimetidine after 2 hours in 0.1N hydrochloric acid; (b) releases at least 60% of cimetidine after 2 hours in 0.1N hydrochloric acid and a further 2 hours in dissolution medium of pH 60; and, (c) releases at least 90% cimetidine after 2 hours in 0.1N hydrochloric acid, and a further 1 hour in a dissolution medium of pH 6.8.

5. A dosage form according to claim 3 wherein the buffer comprises citric, tartaric, benzoic or sorbic acids, alkali metal salts thereof, alkali metal phosphates or mixtures thereof.

6. A dosage form according to claim 5 wherein the buffer comprises a mixture of monosodium citrate and disodium citrate.

7. A dosage form according to claim 2 wherein the amount of buffer is between 0.01 to 5 moles per mole of cimetidine.

8. A dosage form according to claim 7 wherein the amount of buffer is between 0.1 to 0.5 moles per mole of cimetidine.

9. A dosage form according to claim 1 wherein the cimetidine is in the form of its hydrochloride.

10. A dosage form according to claim 2 wherein the cimetidine is in the form of its hydrochloride.

11. A dosage form according to claim 1 wherein the release-delaying substance comprises a coating agent selected from methyacrylic acid copolymers, polymeric methacrylates or mixtures thereof, hydroxypropyl methylcellulose phthalate, cellulose acetate phthalate, ethyl cellulose or polyvinyl acetate phthalate, or mixtures thereof.

12. A dosage form according to claim 2 wherein the release-delaying substance comprises a coating agent selected from methacrylic acid copolymers, polymeric methacrylates or mixtures thereof, hydroxypropyl methylcellulose phthalate, cellulose acetate phthalate, ethyl cellulose or polyvinyl acetate phthalate, or mixtures thereof.

13. A dosage form according to claim 11 where the release-delayed substance comprises:

|  | % (w) |
| --- | --- |
| Coating agent | 40 to 100 |
| Plasticiser | 0 to 20 |
| Lubricant | 0 to 40 |
| Film disintegrating agent | 0 to 40 |

14. A dosage form according to claim 12 where the release-delayed substance comprises:

|  | % (w) |
| --- | --- |
| Coating agent | 40 to 100 |
| Plasticiser | 0 to 20 |
| Lubricant | 0 to 40 |
| Film disintegrating agent | 0 to 40 |

15. A dosage form according to claim 13 wherein the coating agent is a co-polymer of polymethacrylic acid and acrylic acid esters that is soluble in intestinal juice from pH 5.5 upwards.

16. A dosage form according to claim 14 wherein the coating agent is a co-polymer of polymethacrylic acid and acrylic acid esters that is soluble in intestinal juice from pH 5.5 upwards.

17. A dosage form according to claim 15 wherein the release-delaying substance is present in an amount of approximately 2 to 30% (w/w) relative to the uncoated dosage form.

18. A dosage form according to claim 16 wherein the release-delaying substance is present in an amount of approximately 2 to 30% (w/w) relative to the uncoated dosage form.

19. A delayed-release oral dosage form comprising cimetidine or a pharmaceutically acceptable acid addition salt thereof and optionally a buffer that is capable of generating a pH in the range 3.5 to 6 in a 1% aqueous solution, coated with a release-delaying substance in an amount of 2 to 30% (w/w) relative to the uncoated dosage form, the release-delaying substance comprising:

|  | % (w) |
| --- | --- |
| Coating agent | 40 to 100 |
| Plasticiser | 0 to 20 |
| Lubricant | 0 to 40 |
| Film disintegrating agent | 0 to 40 |

20. A dosage form according to claim 19 wherein the coating agent is a copolymer of polymethacrylic acid and acrylic acid esters, hydroxypropyl methyl cellulose phthalate, cellulose acetate phthalate polyvinyl acetate phthalate or a mixture thereof.

21. A dosage form according to claim 19 wherein the coating agent is a copolymer of polymethacrylic acid and acrylic acid esters that is soluble in intestinal juice from pH 5.5 upwards.

22. A dosage form according to claim 19 which comprises a buffer that is capable of generating a pH of 4 to 4.2 in a 1% aqueous solution.

23. A dosage form according to claim 22 wherein the comprises a mixture of monosodium citrate and sodium citrate.

24. A multi-phase medicament comprising an immediate-release phase containing cimetidine or a pharmaceutically acceptable acid addition salt thereof and at least one delayed-release phase comprising a dosage form according to claim 1.

25. A multi-phase medicament comprising an immediate-release phase containing cimetidine or a pharmaceutically acceptable acid addition salt thereof and at least one delayed-release phase comprising a dosage form according to claim 2.

26. A multi-phase medicament comprising an immediate-release phase containing cimetidine or a pharmaceutically acceptable acid addition salt thereof and at least one delayed-release phase comprising a dosage form according to claim 19.

27. A medicament according to claim 24 wherein the immediate- and delayed-release phases are combined in a single dosage form.

28. A medicament according to claim 25 wherein the immediate- and delayed-release phases are combined in a single dosage form.

29. A medicament according to claim 26 wherein the immediate- and delayed-release phases are combined in a single dosage form.

30. A medicament according to claim 27 wherein the delayed-release phase and immediate- release phase are present in a ratio of 5:1 to 1:1.

31. A medicament according to claim 28 wherein the delayed-release phase and immediate- release phase are present in a ratio of 5:1 to 1:1.

32. A medicament according to claim 29 wherein the delayed-release phase and immediate- release phase are present in a ratio of 5:1 to 1:1.

33. A medicament comprising a delayed-release dosage form as defined in claim 1 and a further therapeutic agent which is in a form which enables it to be released in the stomach.

34. A medicament comprising a delayed-release dosage form as defined in claim 2 and a further therapeutic agent which is in a form which enables it to be released in the stomach.

35. A medicament comprising a delayed-release dosage form as defined in claim 19 and a further therapeutic agent which is in a form which enables it to be released in the stomach.

* * * * *